US009820827B2

(12) United States Patent
Feine

(10) Patent No.: US 9,820,827 B2
(45) Date of Patent: Nov. 21, 2017

(54) ABLATION METHOD AND DEVICE

(76) Inventor: James Feine, Bellaire, TX (US)

( * ) Notice: Subject to any disclaimer, the term of this patent is extended or adjusted under 35 U.S.C. 154(b) by 57 days.

(21) Appl. No.: 13/495,281

(22) Filed: Jun. 13, 2012

(65) Prior Publication Data
US 2013/0337404 A1 Dec. 19, 2013

(51) Int. Cl.
A61C 1/07 (2006.01)
A61C 3/025 (2006.01)
A61C 17/20 (2006.01)

(52) U.S. Cl.
CPC .............. A61C 3/025 (2013.01); A61C 17/20 (2013.01)

(58) Field of Classification Search
CPC ........... A61C 17/20; A61C 15/00; A61C 3/03; A61C 17/320068
USPC ..... 433/86, 81, 224, 216, 29, 119, 118, 166, 433/20, 128, 162; 606/169
See application file for complete search history.

(56) References Cited

U.S. PATENT DOCUMENTS

| 3,828,770 | A | * | 8/1974 | Kuris et al. ................... 601/142 |
| 3,924,335 | A | * | 12/1975 | Balamuth et al. ............ 433/119 |
| 4,116,239 | A | * | 9/1978 | Ewen ........................ 128/200.16 |
| 4,331,422 | A | * | 5/1982 | Heyman ........................ 433/125 |
| 4,820,152 | A | * | 4/1989 | Warrin et al. ................... 433/86 |
| 5,013,241 | A | * | 5/1991 | von Gutfeld et al. .......... 433/86 |
| 5,055,043 | A | * | 10/1991 | Weiss et al. ................... 433/86 |
| 5,125,837 | A | * | 6/1992 | Warrin et al. ................... 433/98 |
| 5,213,619 | A | * | 5/1993 | Jackson et al. ................... 134/1 |
| 5,419,703 | A | * | 5/1995 | Warrin et al. ................. 433/216 |
| 5,913,856 | A | * | 6/1999 | Chia et al. ........................ 606/41 |
| 6,322,583 | B1 | * | 11/2001 | Tu et al. ............................ 607/96 |
| 6,522,930 | B1 | * | 2/2003 | Schaer et al. ................... 607/101 |
| 6,722,882 | B2 | * | 4/2004 | Buchanan ...................... 433/119 |
| 7,044,737 | B2 | * | 5/2006 | Fu ................................... 433/119 |
| 8,221,117 | B2 | * | 7/2012 | Rizoiu et al. ................... 433/81 |
| 8,235,719 | B2 | * | 8/2012 | Ruddle et al. .................. 433/81 |
| 2002/0040198 | A1 | * | 4/2002 | Rahman et al. .................. 601/2 |
| 2006/0020310 | A1 | * | 1/2006 | Loebel et al. ................... 607/89 |
| 2006/0234182 | A1 | * | 10/2006 | Ruddle et al. .................. 433/81 |
| 2006/0264897 | A1 | * | 11/2006 | Lobl et al. ..................... 604/506 |
| 2009/0075229 | A1 | * | 3/2009 | Rizoiu et al. ................... 433/29 |

(Continued)

OTHER PUBLICATIONS

Vive K. Bains, Ranjana Mohan and Rhythm Bains, Application of ultrasound in periodontics: Part I, J Indian Soc Periodontol. May-Aug. 2008; 12(2): 29-33. doi: 10.4103/0972-124X.44087 http://www.ncbi.nlm.nih.gov/pmc/articles/PMC2813558/.*

(Continued)

Primary Examiner — Cris L Rodriguez
Assistant Examiner — Mirayda A Aponte
(74) Attorney, Agent, or Firm — Daniel N. Lundeen; Lundeen & Lundeen PLLC

(57) ABSTRACT

A method relating to inserting an ultrasonic oscillatory dental tip into a gingival sulcus of a patient proximate to a subgingival tooth surface, and ultrasonically oscillating the dental tip while supplying a fluid to a porous surface of the dental tip to space the dental tip surface from the subgingival tooth surface to inhibit contact therebetween while debriding biofilm from the tooth surface. A dental tool relating to a tip body having first and second ends, the first end coupleable to a dental delivery device; an internal fluid flow passage through the tip body disposed between the first end and the second end; the second end having a dental tip surface in fluid communication with the internal fluid flow passage.

23 Claims, 7 Drawing Sheets

(56) References Cited

U.S. PATENT DOCUMENTS

2011/0117517 A1* 5/2011 Bergheim et al. .............. 433/81
2012/0270177 A1* 10/2012 Nakashima et al. ............ 433/86

OTHER PUBLICATIONS

Bains, Vivek et al., Application of ultrasound in periodontics Part II, J Indian Soc Periodontol. Sep.-Dec. 2008; 12(3): 55-61, doi: 10.4103/0972-124X.44096, http://www.ncbi.nlm.nih.gov/pmc/articles/PMC2813560/#!po=76.6667].

* cited by examiner

ABLATION METHOD AND DEVICE

BACKGROUND

Biofilms present on teeth, in particular subgingival biofilms may be removed to promote proper oral hygiene. Biofilms may be removed by physical abrasion, which may cause discomfort to the patient and erosion of the tooth surface.

SUMMARY

The present disclosure is generally directed to a method of and a dental delivery tip useful for non-contact ablation of biofilms.

In an embodiment, a method comprises inserting an ultrasonic oscillatory dental tip into a gingival sulcus of a patient proximate to a subgingival tooth surface and ultrasonically oscillating the dental tip while supplying a fluid to a surface of the dental tip opposing the subgingival tooth surface to space the dental tip surface from the subgingival tooth surface to inhibit contact therebetween. In embodiments, the oscillation cavitates the fluid and/or forms an acoustic pressure wave to facilitate biofilm removal. In an embodiment, a frequency of the ultrasonic oscillation of the dental tip, a flow rate of the fluid, or a combination thereof may be selected such that at least a portion of a biofilm present on the subgingival tooth surface is ablated by the fluid.

In an embodiment, a dental tip comprises a tip body having first and second ends, the first end coupleable to a dental delivery device, an internal fluid flow passage through the tip body disposed between the first end and the second end, the second end having a dental tip surface in fluid communication with the internal fluid flow passage.

DETAILED DESCRIPTION

Detailed embodiments are disclosed herein. However, it is understood that the disclosed embodiments are merely exemplary of the disclosure, which may be embodied in various forms. Specific structural and functional details disclosed herein are not intended to be limiting, but merely illustrations that can be modified within the scope of the attached claims.

Figure 1:
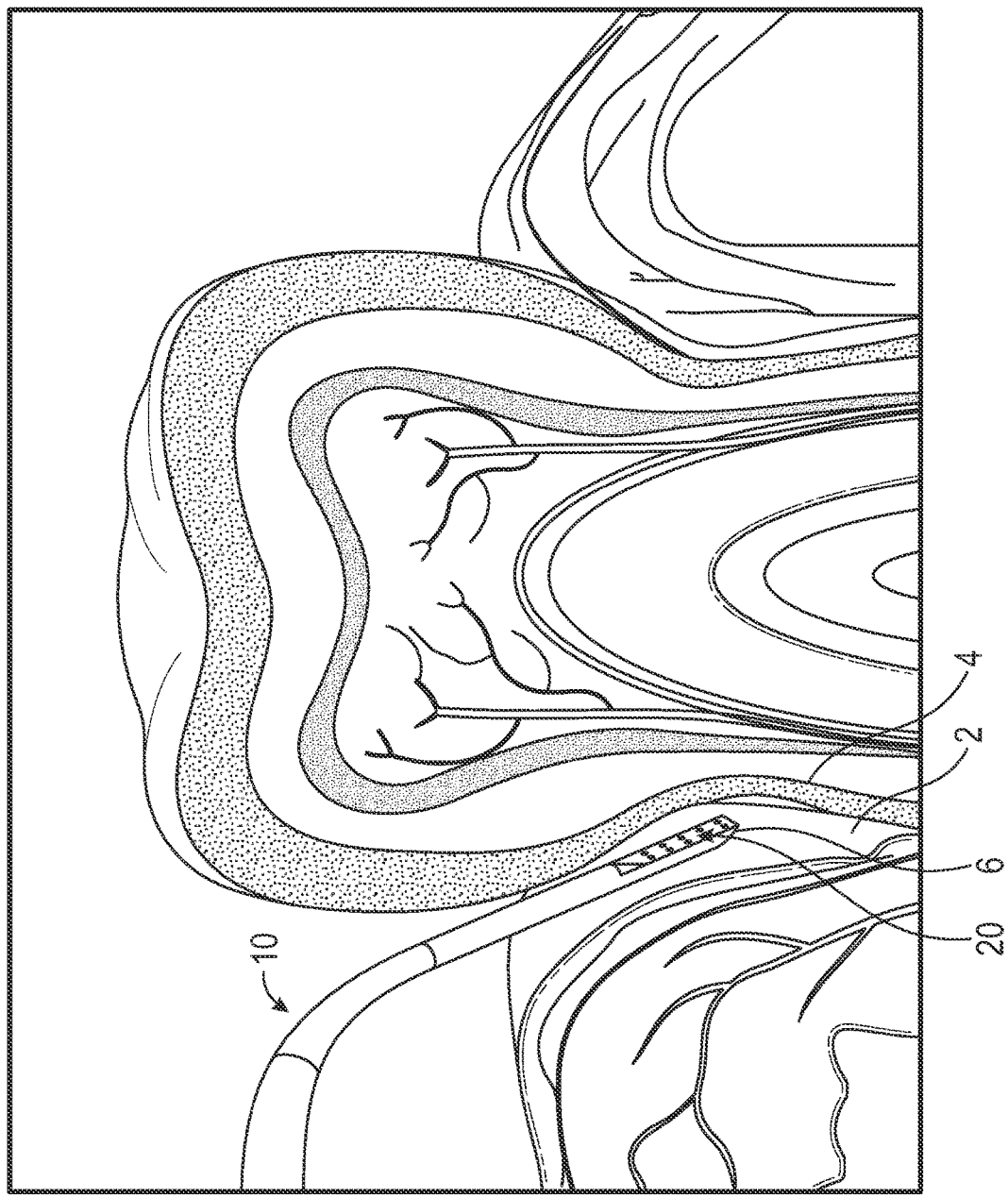
FIG. 1 shows utilization of the dental delivery tip according to an embodiment of the present disclosure.

As shown in FIG. 1, in an embodiment, a dental hygienic method comprises inserting an ultrasonic oscillatory dental tool, also referred to herein as a dental tip 10, into a gingival sulcus 2 of a patient proximate to a subgingival tooth surface 4 and ultrasonically oscillating the dental tip 10 while supplying a fluid to a surface 20 of the dental tip 10 opposing the subgingival tooth surface 4 at a rate and pressure to help space the dental tip surface 20 from the subgingival tooth surface 4 and thereby inhibit contact therebetween. In an embodiment, the operator presses the tip surface 20 against the tooth surface 4 with a pressure sufficiently light to avoid direct tooth-instrument contact. In an embodiment, the oscillation may optionally produce cavitation in the fluid 6, and/or optionally impinge an acoustic pressure onto the tooth surface.

Figure 2A:
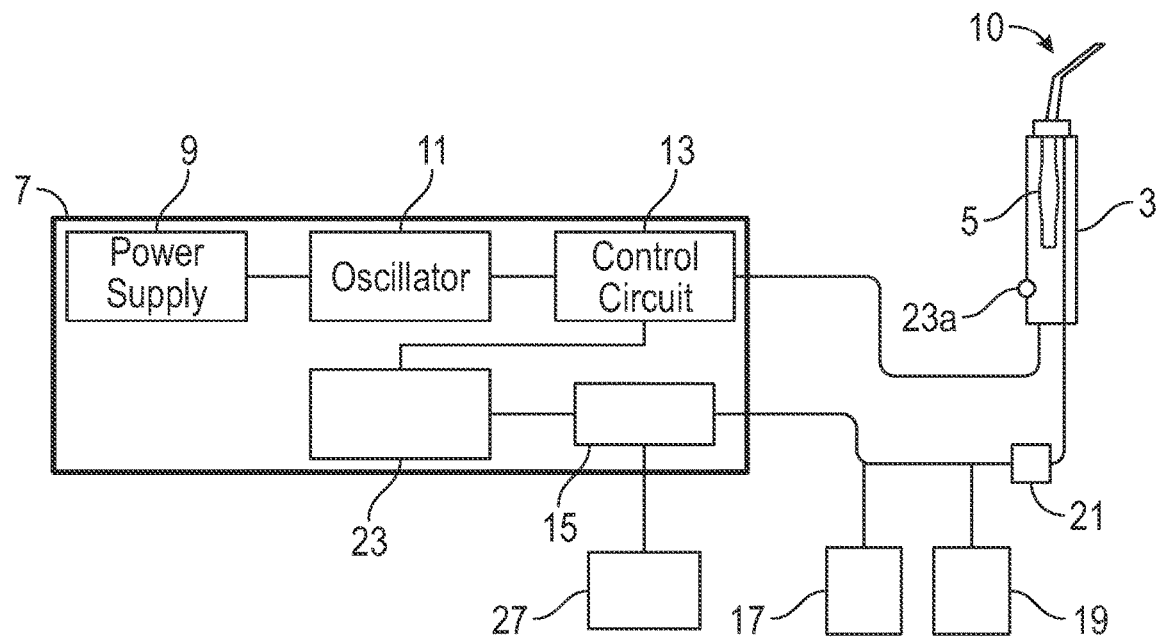
FIG. 2A shows a block diagram of a dental delivery device according to an embodiment of the present disclosure coupled to a handpiece.

As shown in FIG. 2A, the dental tool 10, also referred to herein as a dental tip, may be coupled to a hand-held instrument 3, often referred to as a hand piece, which are readily known to one of minimal skill in the art. An operator may use a powered hand-held instrument 3 to deliver dental services to a patient. This hand-held dental delivery device 3 may be powered by electricity or some other energy source. Examples of such dental devices include ultrasonic scalers, power polishers, and instruments for providing abrasion.

As shown in FIG. 2A, the dental tool according to an embodiment of the instant disclosure may further comprise a handpiece 3, which may comprise a piezoelectric element, and/or a magnetostrictive element, generally referred to as 5. In an embodiment, the dental tool may further comprise a control system 7 comprising an ultrasonic power supply 9 which may include an oscillator 11 and control circuitry 13, a fluid supply 15 in fluid communication with the internal fluid flow passage 16 of the dental tip (see FIG. 3), a fluid supply pressure controller 17, a fluid supply flow rate controller 19, a fluid filter 21, an operator interface 23 and/or 23a, and/or the like.

Figure 2B:
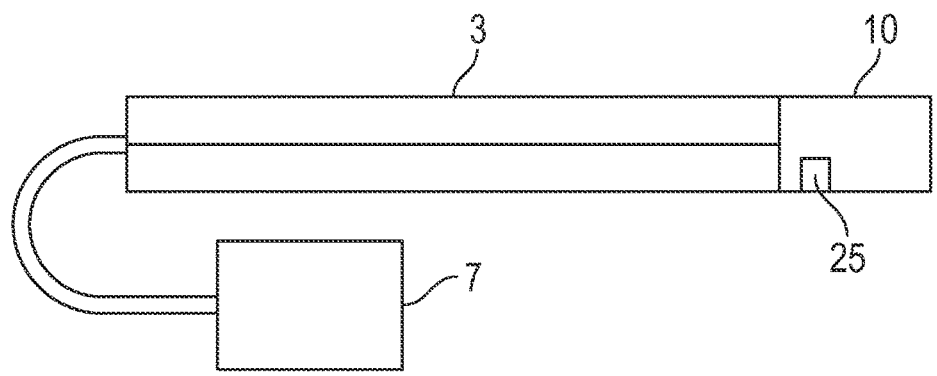
FIG. 2B shows a block diagram of a dental delivery device according to an embodiment of the present disclosure coupled to a handpiece.

As shown in block diagram form in FIG. 2B, in an embodiment, the dental tool may further comprise one or more electrical devices 25 located thereon, wherein the electrical device 25 comprises one or more of a piezoelectric crystal stack, caries detector, cancer detector, temperature detector, density detector, strain detector, pressure detector, flow rate detector, conductivity detector, power level detector, illumination light, curing light, spectroscopic detector, prophylactic dispenser, medicament dispenser, imaging device, operational controller, microprocessor, memory module, communication device, electromagnet, ac to dc converter, radio frequency identification tag, or a combination thereof.

Various functions of the hand-held dental delivery devices may be controlled by the operator through the operational controller 23 including the power delivered to these hand-held devices by using an operator control input mechanism such as a switch, button, or foot pedal. The operator may be further enabled, via an operator control input mechanism 23a located on the handpiece, to adjust the power level during a dental procedure within an optimum safe power range including the minimum and maximum energy level sent to the handpiece 3.

As shown in FIG. 2A, fluid delivery through a hand-held powered dental delivery device 3 may be controlled by a fluid supply pressure controller 17, a fluid supply flow rate controller 19, and/or the like which may include a solenoid and a manual metering valve and/or pressure regulator. The solenoid may control the on/off action of the fluid flow, and the metering valve/regulator may control the flow rate. In an embodiment, the solenoid may be controlled by a foot pedal switch, and the flow rate may be manually controlled by a valve mounted on the unit, remotely on the dental cart or chair, or integrated into the handpiece. The operator thus may be required to use his/her hands to make adjustments to fluid delivery in addition to using the dental delivery device during the dental procedure. For instance, if a dental device requires more power to debride a particular surface, heat may be built up in the dental device and at the tooth site, thus requiring the operator to manually increase the flow of water for cooling, irrigation, or a combination thereof. In another example, the operator may need to manually increase the flow of a medicament from a medicament distribution system 27 while the hand-held dental device is in proximity to the site of intended application of the medicament, and decrease the flow as the instrument moves away from the site.

In an embodiment, the handpiece 3 is an ultrasonic handpiece which may include an oscillation driver such as a magnetostrictive oscillator, a piezo oscillator, or the like 5, coupled to the dental tip 10. Sound waves produced via ultrasonic oscillation of the dental tip comprise two actions; an expansion cycle during which the liquid molecules are being pulled apart, and a compression cycle, during which the molecules are being compressed. In an embodiment, the expansion cycle of the wave has enough energy to overcome the forces which hold the molecules of liquid together and a cavity is produced. Immediately following the expansion cycle, the compression cycle follows, rapidly compressing the cavities created. Accordingly, in an embodiment, ultrasonic oscillation of the dental tip results in cavitation within the fluid supplied through a porous surface of the dental tip. Cavitation refers to the momentary creation of vacuum "tears" commonly referred to as "bubbles" in the fluid which immediately and violently implode to produce millions of microscopic jets of liquid which gently clean and ablate the subgingival surfaces. In addition, local temperatures associated with the implosion events have been shown to be as high as 10,000 degrees Celsius, and the pressure produced during cavitation may be as high as 70 MPa (10,000 PSI). These tears or cavities are created millions of times each second to gently remove contaminants and perform other debridement functions without damage to the surrounding tissues or the subgingival root surface. Ultrasonic oscillation is generally between 10 KHz and 50 KHz, resulting in cavities being generated 10,000 to 50,000 times each second.

During cavitation, an imploding cavity folds inward and produces a jet of liquid directed away from the center of the cavity. Thousands of times each minute, the tissues in contact with the ultrasonically oscillated fluid are contacted by these implosions, although the cleaning action produced is rather gentle. Although these cavities are produced by the thousands, the distribution of these cavities is determined by the ultrasonic frequency in operation. In an embodiment, the ultrasonic dental tip produces a cleaning action that is distributed as a series of equidistant bands of activity relative to the porous surface of the dental tip. These bands are referred to herein as standing waves, and cleaning action between standing waves is only a fraction of the energy which is produced at a standing wave location. Accordingly, in an embodiment, the appropriate ultrasonic frequency is selected to achieve the desired level of cavitation to produce the intended result. This selection may be in the form of tuning of the tip in relation to the ultrasonic oscillation frequency, the flow of fluid to the porous surface of the dental tip, the temperature of the fluid, the composition of the fluid, and/or the like. In an embodiment, the frequency is selected to produce a distribution of cavitation which ensures that the subject surface is successfully cleaned of biofilm.

In an embodiment, the power setting for the dental tip would be less than 25 watts, preferably less than 10 watts, with from 4 to 6 watts being still more preferred.

Accordingly, the ultrasonic frequency in use determines how often cavities are produced per unit of time, the size of the cavity, the distribution of cleaning action, and the force behind cavitational implosion. The higher the frequency, the shorter the compression and expansion cycles, which result in cavities being produced which are smaller in comparison to cavities produced at lower frequency oscillations since there is less time to increase the size of the cavity during the expansion cycle. The end result is a more gentle cleaning action at higher ultrasonic frequencies.

In an embodiment, the ultrasonic oscillation of the fluid supplied to or through the porous dental tip surface, produces an acoustic pressure. In an embodiment, the acoustic pressure is a near field acoustic pressure produced in the fluid supplied to the porous surface of the dental tip with the near field determined relative to the porous surface. In the near field region, the sound pressure and acoustic particle velocity are out of phase. In an embodiment, the near field distance is a distance from the porous surface of the dental tip to a point equal to about a wavelength of sound. In an embodiment, the near field distance is equal to the velocity of sound in the fluid, typically water with a velocity of 1540 m/s, divided by the frequency. In an embodiment, the acoustic pressure produced is sufficient to inhibit contact between the dental tip and subgingival tooth surface, or the surface directly opposite the porous surface of the dental tip. In an embodiment, the fluid forms a fluid cushion to inhibit contact between the dental tip and the sub-gingival tooth surface.

In an embodiment, a frequency of the ultrasonic oscillation of the dental tip, a flow rate of the fluid supplied to the dental tip surface, or a combination thereof is selected such that at least a portion of a biofilm present on the subgingival tooth surface is ablated by the cavitation in the fluid. In an embodiment, the flow rate of the fluid supplied to the porous surface is from about 10 microliters per minute to about 10 milliliters per minute.

In an embodiment, the method may be utilized as part of a treatment regime for periodontal tissue having an indication of one or more pathological conditions including a periodontal biofilm mass, periapical endodontic lesions, endo-perio lesions, gingivitis, inflammation of gingival tissue, periodontitis, progressive loss of ligament, cementum or alveolar bone support to teeth. In an embodiment, the treated tissue may have one or more conditions requiring treatment including ridge augmentation for cosmetic, prosthetic or implantation of teeth; to assist osteoblastic and osteoclastic processes in orthodontia; regeneration of alveolar bone surrounding loose teeth implants regeneration of structures supporting the teeth including regeneration of structures supporting teeth including gingival, periodontal ligament, cementum and alveolar bone. In an embodiment, the method according to the instant disclosure may be used for prevention and/or treatment of periodontal disease and may be used with debridement.

As used herein, debridement may include ultrasonic debridement wherein a relatively blunt metal tipped instrument is applied to the root surface below the gum line. The metal tip vibrates at ultrasonic frequencies and breaks the calculus (tartar) attachment to the root of the tooth. Calculus is the hardened substance that attaches to both the tooth structure above and below the gum line. The ultrasonic tip is used in both areas. Patients with periodontal disease typically have sub and supra-gingival calculus, but not always. Debridement may also include the surgical removal of lacerated, devitalized, or contaminated tissue. This includes removal of tartar above and/or beneath the gum, generally referred to as scaling, and root planning and in more advanced conditions may necessitate periodontal surgery or complete debridement of the roots and re-contouring of the hard and soft tissue to arrest the disease process or to restore lost bone.

As used herein, biofilms include the combination of the nearly 25,000 different forms of aerobic, anaerobic and microaerobic organisms commonly referred to as dental plaque, as well as the byproducts and residues produced thereby.

In an embodiment, the fluid is supplied to the porous surface from an internal fluid passage located in the dental tip. In an embodiment, the fluid passage is in fluid communication with a fluid supply source, which may include a pump, various controls, and the like. In an embodiment, the fluid is degassed prior to supplying the fluid to the porous surface of the dental tip. The amount of dissolved gasses within the fluid affects ultrasonic cavitation. Dissolved gasses are a compressible medium which act as a "shock absorber" to ultrasonic energy being emitted. Although cavitation will be present, its power available for cavitation is reduced. Fluids which have been degassed produce 25-50% more cleaning effect than fluids containing dissolved gasses. In an embodiment, degassing of the fluid may include subjecting the fluid to pressure reduction, heating, membrane degasification, substitution by inert gas, addition of reductant, freeze-pump-thaw cycling, and the like, prior to supplying the fluid though the porous surface of the dental tip. Degassing of the fluid prior to delivery may also be accomplished by any of the methods known to one of minimal skill in the art.

In an embodiment, the fluid supplied to the surface of the dental tip surface may be filtered. In an embodiment, the filter may be a sintered bronze or similar filter with 25-30 micron openings, or openings sufficient to prevent clogging of the porous surface.

In an embodiment, the fluid supplied to the porous surface comprises one or more additives which may include a desensitizer, a flavorant, and/or a medicament. In an embodiment, the medicament may include a bis-biguanide, an essential oil, a quaternary ammonium compound, a fluoride, an antibiotic, an oxygenating agent, an antiseptic, an enzyme, a plant alkaloid, sodium hexametaphosphate, sodium etedronate, saline, a salt, or a combination thereof. In an embodiment, a bis-biguanide may include chorhexidine, alexidine, octeudine, bis-pyridines, and the like. Examples of essential oils include oil of clove, thujone, eucalyptus oil, rose oil, peppermint, oil of lavender, and the like. In an embodiment, quaternary ammonium compounds include cetyl pyridium chloride, benzalkonium chloride, and the like. In an embodiment, fluorides include sodium fluoride, stannous fluoride, organic amine fluorides, and the like. In an embodiment, antibiotics may include penicillin, tetracycline, vancomycin, kanamycin, psiramyicin, actinomycin, erythromyicin, niddamycin, streptomycin, bacitrancin, gramicidin, and the like. In an embodiment, oxygenating agents may include peroxides, hydrogen peroxide, urea peroxide, ozone, and the like. In an embodiment, antiseptics may include iodine, providone iodine, chloramine T, and the like. In an embodiment, enzymes may include amylase, mutanase, protease, amylglycosidase, glucose oxidase, and the like. In an embodiment, suitable plant alkaloids may include sanguarine and the like.

Accordingly, the method of treatment may further comprise administering one or more additives and/or medicaments prior to, during or after debridement or subjecting a tissue to a surgical procedure to remove or repair some or all of any defects or degenerative tissues. In an embodiment, the temperature of the fluid supplied to the porous surface may be controlled. The temperature of the fluid may be increased or decreased depending on the intended result, which may include cooling of the dental hand piece the dental tip is attached to, to improve ablation of the subgingival tooth surface, or a combination thereof. In an embodiment, the dental tip may include one or more thermocouples in communication with an external monitor to determine and/or monitor the temperature of the fluid prior to entering the handpiece, emanating from the porous surface of the dental tip, the temperature of the fluid present in the gingival sulcus, or a combination thereof.

In an embodiment, the method may further comprise controlling the composition and/or the amount of the fluid supplied to the porous surface of the dental tip. In an embodiment, one or more fluids, which may include one or more additives or medicaments, may be combined with a carrier fluid controlled by the operator or may be controlled by a control system of the dental hand piece to facilitate ablation of biofilm present in the gingival sulcus, or the like. Suitable additives may include surfactants, cleaners, solvents, and the like. In an embodiment, suction may be required to remove fluid accumulation from mouth and/or to mitigate formation of aerosols. For example, during debridement of the lower jaw, the water or other fluid may pool in the sulcus and need to be removed. However, debridement of the upper mandible allows the fluid to run out more quickly and thus a higher fluid flow rate may be needed along with an increased evacuation of the area.

In an embodiment, the method may further comprise super gingival cleaning of the patient's teeth with a hygienic instrument in contact with a super gingival tooth surface. In an embodiment, the method may further comprise subgingival scaling of the patient's teeth with a hygienic instrument in contact with the subgingival tooth surface.

In an embodiment, the operator may be able to provide input to adjust the flow rate during a dental procedure using the operator control input. Some conditions that require flow rate adjustments are detectable only by the operator, for example, the need for a greater amount water to flush a bigger orifice and a lesser amount for a smaller orifice. Other conditions detectable by only the operator may include an increased amount of debris that requires more vigorous flushing, or a patient gagging and requiring cessation of the fluid flow. Additionally, an operator may wish to augment or override the microprocessor's flow control algorithm to adjust the flow for his/her own personal preferences during a procedure. In an embodiment, an operator flow control input device mechanism may be a foot pedal. As the operator increases pressure on the foot pedal, the increase in pressure may be detected by a microprocessor or other control system and the fluid flow rate may increase, and vice versa. The foot pedal may be the same unit as the operator power control input mechanism or it may be a separate unit. Other embodiments of an operator flow control input mechanism may also be possible, such as a button on the handpiece, a dial on the base unit, and/or an emergency stop switch. The operator may be able to adjust the flow within a designated normal operating range.

Figure 3A:
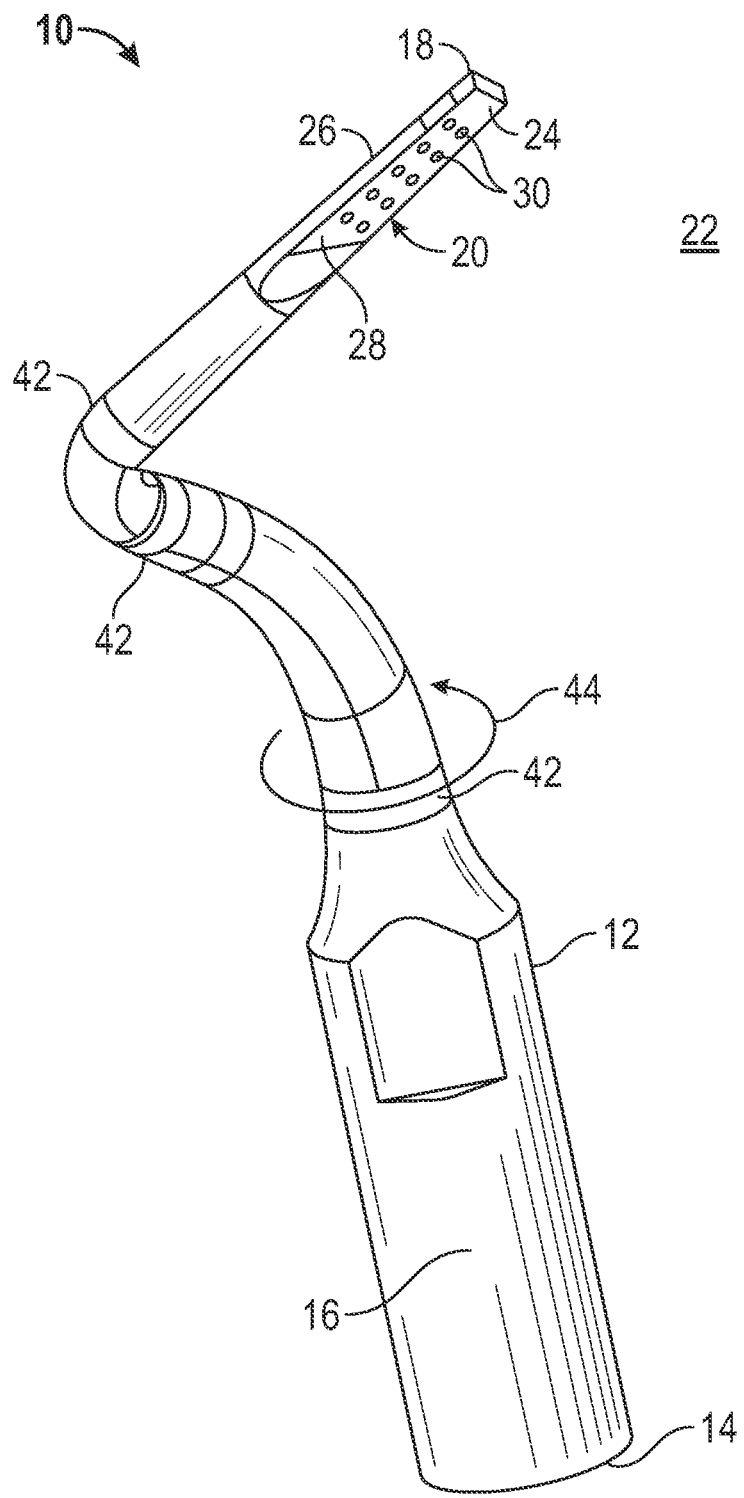
FIG. 3A is a perspective view of a dental delivery tip according to an embodiment of the present disclosure.
Figure 3B:
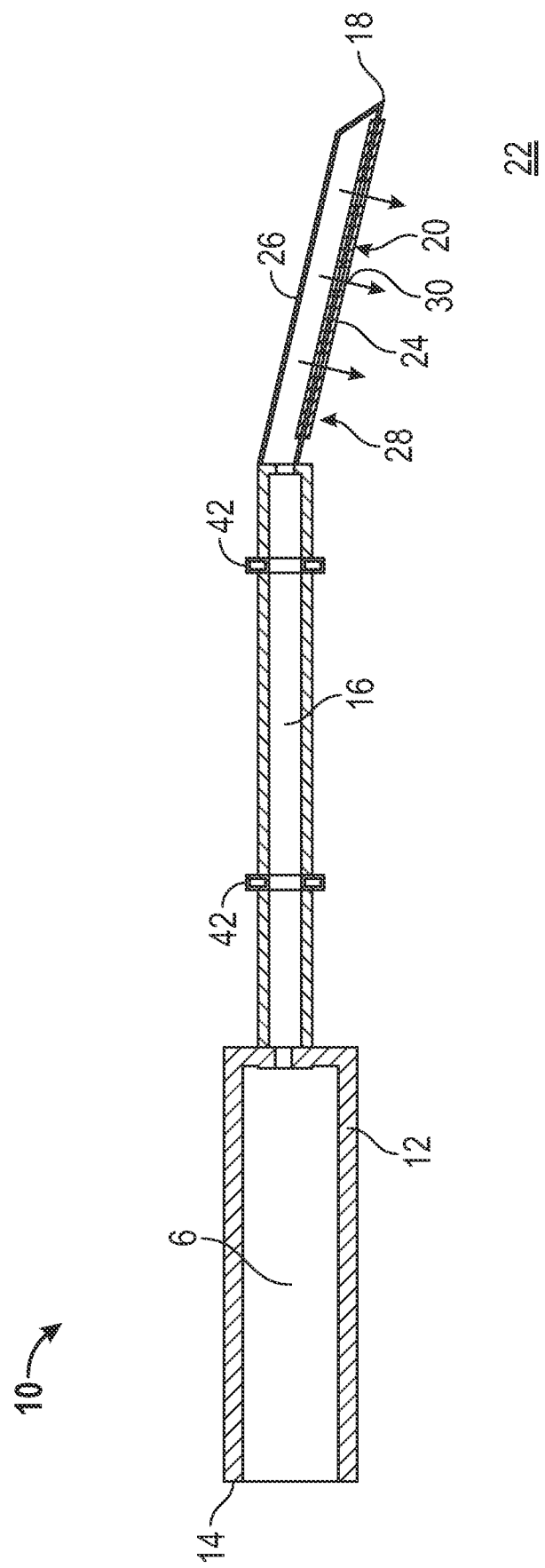
FIG. 3B is a cross-sectional view of the embodiment shown in FIG. 3A along a centerline of the dental delivery tip.

Turning to FIG. 3, in an embodiment, a dental tip 10 according to the instant disclosure comprises a tip body 12 having first and second ends, the first end 14 coupleable to a dental delivery device; an internal fluid flow passage 16 through the tip body 12 disposed between the first end 14 and the second end 18; the second end 18 having a dental tip surface 20, which may be a porous surface, which is in fluid communication with the internal fluid flow passage 16. In an embodiment, the second end 18 comprises a porous surface 20 through which the internal fluid flow passage 16 is in fluid communication with an exterior environment 22.

In an embodiment, second end 20 comprises a front side 24 and a back side 26, the front side 24 comprising a planar surface, an oblique surface, a concave surface, a convex surface, or a combination thereof 28 comprising the porous surface 20. In an embodiment, the second end 20 is dimensioned and arranged to fit within the gingival sulcus of a patient, and thus may comprise a relatively thin and flat surface, which may taper from one end to another. In an embodiment, the tip may be wedge shaped narrower at the end and thicker at the base. In an embodiment, the second end may have a maximum cross-sectional thickness of less than 5 mm, preferably less than 4 mm, preferably less than 3 mm, preferably less than 2 mm, with a maximum width of less than 10 mm, preferably less than 8 mm, preferably less than 6 mm, preferably less than 5 mm preferably less than 4 mm preferably less than 3 mm.

Figure 4:
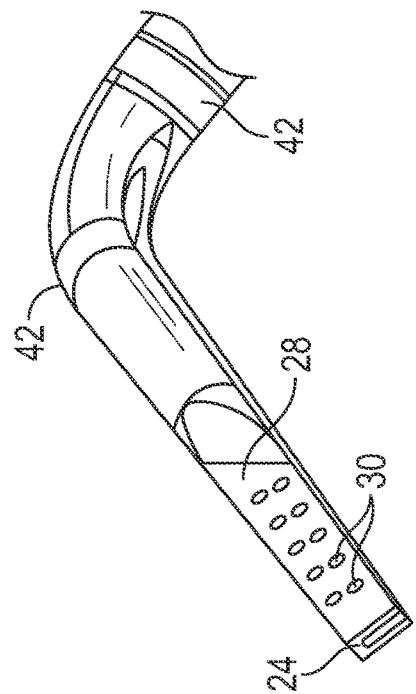
FIG. 4 is a perspective view of a dental delivery tip according to another embodiment of the present disclosure.
Figure 4A:
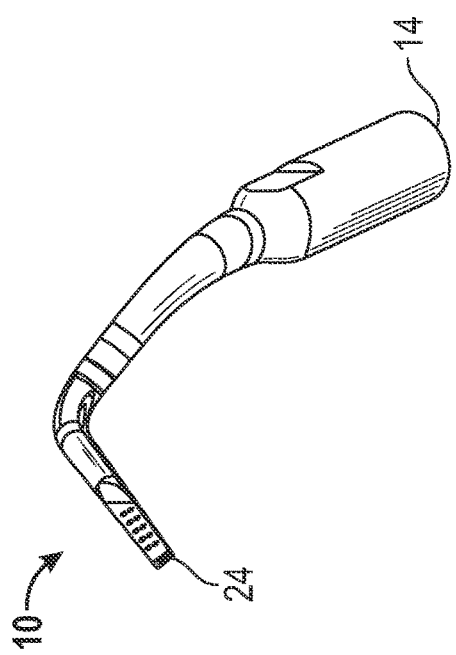
FIG. 4A is a perspective view of Detail A shown in FIG. 4.

As shown in FIGS. 4 and 4A, in an embodiment, the porous surface 20 comprises one or a plurality of openings 30 disposed through at least a portion of the second end 24.

Figure 5A:
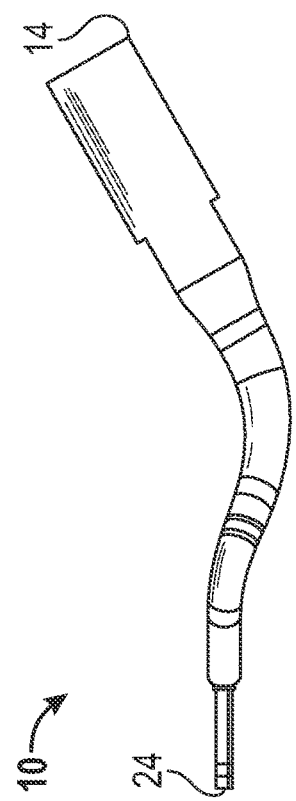
FIG. 5A is a view of a dental delivery tip in one of various conformations according to an embodiment of the present disclosure.
Figure 5B:
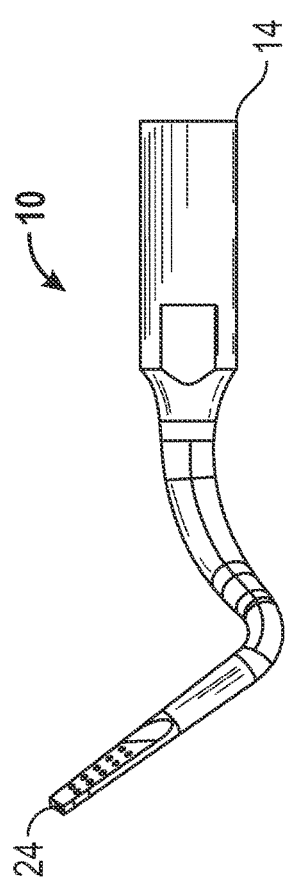
FIG. 5B is a view of a dental delivery tip in another one of various conformations according to an embodiment of the present disclosure.
Figure 6A:
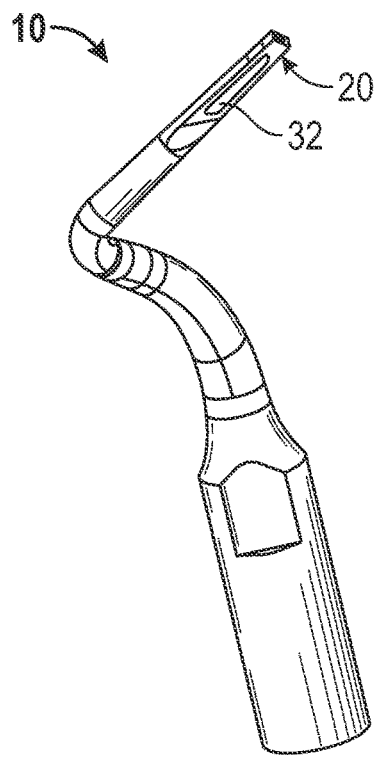
FIG. 6A is a perspective view of an alternative embodiment of a dental tip according to the present disclosure.
Figure 6B:
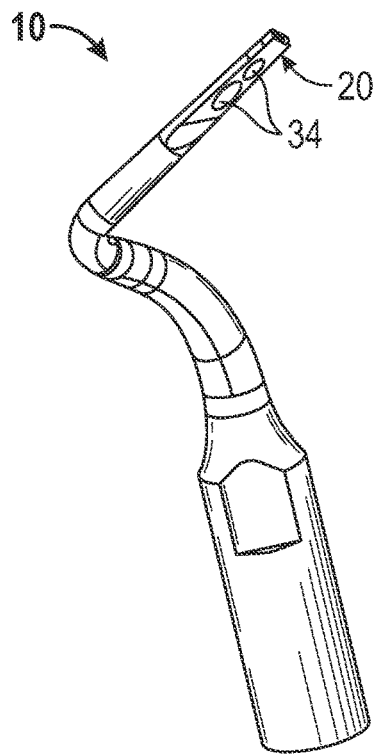
FIG. 6B is a perspective view of another alternative embodiment of a dental tip according to the present disclosure.
Figure 6C:
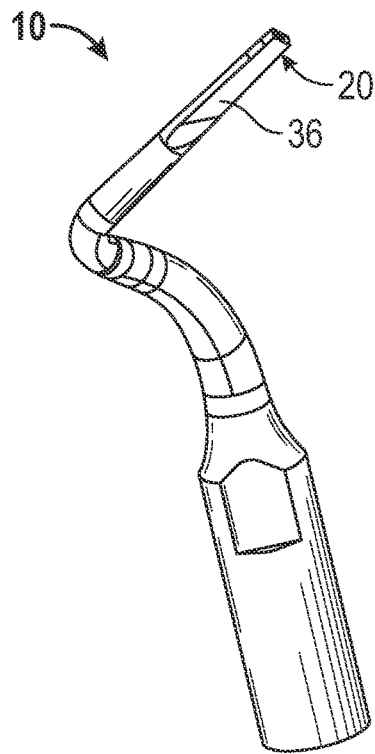
FIG. 6C is a perspective view of another alternative embodiment of a dental tip according to the present disclosure.
Figure 6D:
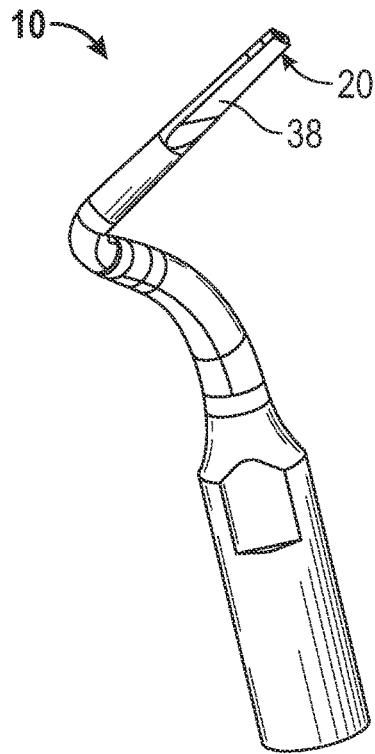
FIG. 6D is a perspective view of another alternative embodiment of a dental tip according to the present disclosure.
Figure 6E:
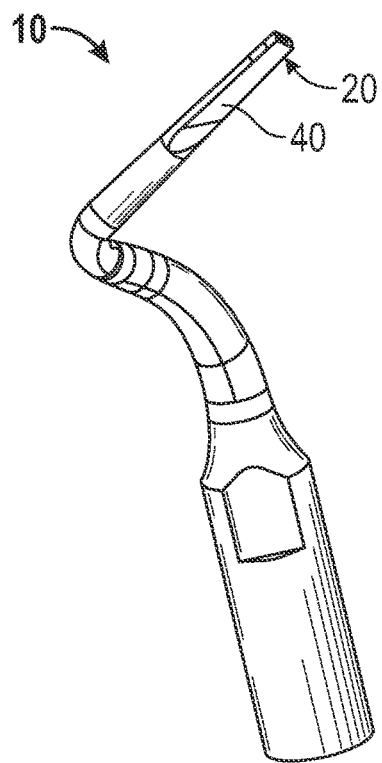
FIG. 6E is a perspective view of another alternative embodiment of a dental tip according to the present disclosure.
Figure 7:
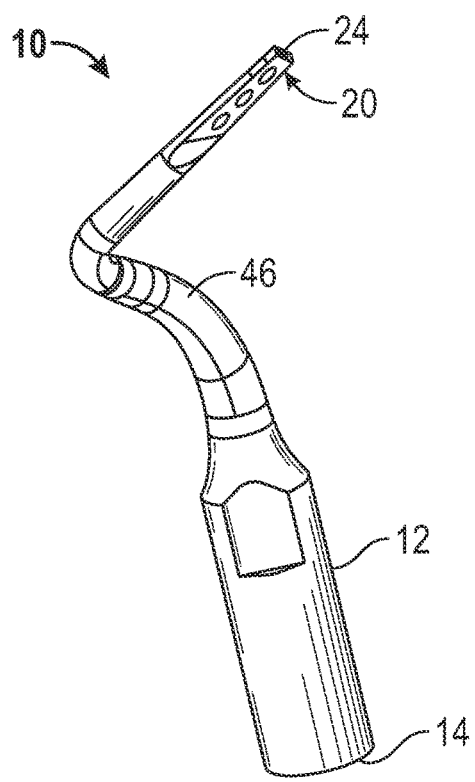
FIG. 7 is a perspective view of alternative embodiments of a dental tip according to the present disclosure.

In an embodiment, the tip body 12 may comprise one or more swivel joints 42 disposed between the first end 14 and the second end 24 to allow at least partial rotation 44 of the second end 24 relative to the first end 14. As shown in the embodiments of FIGS. 5A and 5B, second end 24 may be manipulated in an infinite number of locations relative to first end 14 via rotation about one or more swivel joints 42. In an embodiment, as shown in FIGS. 6A-6E, the porous surface 20 comprises a semi-permeable membrane 32 (FIG. 6A), a glass frit 34 (FIG. 6B), a semi-permeable fused ceramic 36 (FIG. 6C), a woven fabric 38 (FIG. 6D), a non-woven fabric 40 (FIG. 6E), or a combination thereof. As shown in FIG. 7, in an embodiment, at least a portion of the tip body 12 may comprise a flexible conduit 46.

In an embodiment, the dental tip may comprise any metal, metallic alloy, polymeric thermoplastic resin, polymeric thermoset resin, and/or the like, which is suitable for use in a dental tool or device, such as, for example, stainless steel, ABS resin, phenolic resin, nylon, halogenated polyolefin (e.g., polytetrafluoroethylene) or non-halogenated polyolefin resin, or the like. The metallic or polymeric material may be porous or provided with a plurality of openings to the ablation surface. In an embodiment, the dental tool may be constructed to withstand sterilization procedures including autoclaving and other methods known to one of minimal skill in the art. In an embodiment, the dental tip or a detachable portion thereof may be constructed as a single-use device for use as a disposable, replaceable or consumable dental tool, or as a device having a limited number of uses and/or limited autoclavability for disposal after 2, 3, 4, 5 or the like number of uses.

EMBODIMENTS

Accordingly, the embodiments of the instant disclosure may include any one or combination of the following embodiments.

A. A method comprising inserting an ultrasonic oscillatory dental tip into a gingival sulcus of a patient proximate to a subgingival tooth surface; supplying a fluid to a surface of the dental tip opposing the subgingival tooth surface to form a fluid cushion to inhibit contact therebetween; and ultrasonically oscillating the dental tip to debride biofilm from the tooth surface.

B. The embodiment of A wherein the surface of the dental tip is porous.

C. The embodiment of A or B, wherein the fluid is supplied to the porous surface of the dental tip from an internal fluid passage located in the dental tip.

D. The embodiment of A, B, or C, wherein the ultrasonic oscillation of the dental tip produces cavitation in the fluid.

E. The embodiment of A, B, C, or D, wherein a frequency of the ultrasonic oscillation of the dental tip, a flow rate of the fluid supplied to the porous surface of the dental tip, or a combination thereof is selected such that at least a portion of a biofilm present on the subgingival tooth surface is ablated by the cavitation in the fluid.

F. The embodiment of A, B, C, D, or E, wherein the ultrasonic oscillation of the dental tip produces an acoustic pressure between the surface of the dental tip and the subgingival tooth surface.

G. The embodiment of A, B, C, D, E, or F, wherein the fluid supplied to the porous surface comprises an additive, a medicament, or a combination thereof.

H. The embodiment of A, B, C, D, E, F, or G, further comprising controlling the temperature of the fluid.

I. The embodiment of A, B, C, D, E, F, G, or H, wherein the fluid is filtered prior to being supplied to the surface of the surface of the dental tip.

J. The embodiment of A, B, C, D, E, F, G, H, or I, further comprising degassing the fluid prior to supplying the fluid to the dental tip.

K. The embodiment of A, B, C, D, E, F, G, H, I, or J, further comprising controlling the composition of the fluid supplied to the surface of the dental tip.

L. The embodiment of A, B, C, D, E, F, G, H, I, J, or K, further comprising scaling of the patient's teeth with a hygienic instrument in contact with a tooth surface.

M. A dental tool comprising a tip body having first and second ends, the first end coupleable to a dental delivery device; an internal fluid flow passage through the tip body disposed between the first end and the second end; the second end having a dental tip surface in fluid communication with the flow passage.

N. The embodiment of M, wherein the dental tip surface comprises a porous surface.

O. The embodiment of M or N, wherein the porous surface comprises a plurality of openings disposed through at least a portion of the second end.

P. The embodiment of M, N, or O, wherein the porous surface comprises a semi-permeable membrane, a glass frit, a semi-permeable fused ceramic, a woven fabric, a non-woven fabric, or a combination thereof.

Q. The embodiment of M, N, O, or P, wherein the second end comprises a front side and a back side, the front side comprising the dental tip surface.

R. The embodiment of M, N, O, P, or Q, wherein the dental tip surface comprises a planar surface, an oblique surface, a concave surface, a convex surface, or a combination thereof comprising a porous surface.

S. The embodiment of M, N, O, P, Q, or R, wherein the second end is dimensioned and arranged to fit within a gingival sulcus of a patient proximate to a subgingival tooth surface.

T. The embodiment of M, N, O, P, Q, R, or S, wherein the tip body comprises one or more swivel joints disposed between the first end and the second end to allow at least partial rotation of the second end relative to the first end.

U. The embodiment of M, N, O, P, Q, R, S, or T, wherein at least a portion of the tip body comprises a flexible conduit.

V. The embodiment of M, N, O, P, Q, R, S, T, or U, further comprising a handpiece and a piezoelectric element, a magnetostrictive element, or a combination thereof.

W. The embodiment of M, N, O, P, Q, R, S, T, U, or V, further comprising a control system comprising an ultrasonic power supply, a fluid supply in fluid communication with the internal fluid flow passage, a fluid supply pressure controller, a fluid supply flow rate controller, or a combination thereof.

X. The embodiment of M, N, O, P, Q, R, S, T, U, V, or W, further comprising an electrical device located thereon, wherein the electrical device comprises one or more of a piezoelectric crystal stack, caries detector, cancer detector, temperature detector, density detector, strain detector, pressure detector, flow rate detector, conductivity detector, power level detector, illumination light, curing light, spectroscopic detector, prophylactic dispenser, medicament dispenser, imaging device, operational controller, microprocessor, memory module, communication device, electromagnet, ac to dc converter, radio frequency identification tag, or a combination thereof.

The invention is described above in reference to specific examples and embodiments. The metes and bounds of the invention are not to be limited by the foregoing disclosure, which is illustrative only, but should be determined in accordance with the full scope and spirit of the appended claims. Various modifications will be apparent to those skilled in the art in view of the description and examples. It is intended that all such variations within the scope and spirit of the appended claims be embraced thereby.

The invention claimed is:

1. A method comprising:
inserting an ultrasonic oscillatory dental tip into a gingival sulcus of a patient proximate to a subgingival tooth surface to position a surface of the dental tip in opposition to the subgingival tooth surface;
supplying a pressurized fluid through the surface of the dental tip to form a fluid cushion to inhibit contact of the subgingival tooth surface by the surface of the dental tip; and
ultrasonically oscillating the dental tip to ablate biofilm from the subgingival tooth surface while maintaining the fluid cushion.

2. The method of claim 1, wherein the surface of the dental tip is porous and comprises a plurality of openings.

3. The method of claim 2, wherein the fluid is supplied to the plurality of openings of the surface of the dental tip from an internal fluid passage located in the dental tip.

4. The method of claim 1, wherein the ultrasonic oscillation of the dental tip produces cavitation in the fluid.

5. The method of claim 4, wherein a frequency of the ultrasonic oscillation of the dental tip, a flow rate of the fluid supplied to the surface of the dental tip, or a combination thereof is selected such that at least a portion of a biofilm present on the subgingival tooth surface is ablated by the cavitation in the fluid.

6. The method of claim 1, wherein the ultrasonic oscillation of the dental tip produces an acoustic pressure between the surface of the dental tip and the subgingival tooth surface.

7. The method of claim 1, wherein the fluid supplied to the surface of the dental tip comprises an additive, a medicament, or a combination thereof.

8. The method of claim 1, further comprising controlling the temperature of the fluid.

9. The method of claim 1, wherein the fluid is filtered prior to being supplied to the surface of the dental tip.

10. The method of claim 1, further comprising degassing the fluid prior to supplying the fluid to the dental tip.

11. The method of claim 1, further comprising controlling the composition of the fluid supplied to the surface of the dental tip.

12. The method of claim 1, further comprising scaling of the patient's teeth with a hygienic instrument in contact with a tooth surface.

13. A dental tool, comprising:
a tip body having first and second ends, the first end coupleable to a dental delivery device;
an internal fluid flow passage through the tip body disposed between the first end and the second end;
the second end having a flat, porous, ultrasonic dental tip surface comprising a plurality of openings in fluid communication with the internal fluid flow passage, whereby a pressurized fluid can be supplied directly to the ultrasonic dental tip surface to form a fluid cushion to inhibit contact by the ultrasonic dental tip surface with a tooth surface placed in opposition to the ultrasonic dental tip surface;
wherein the second end is dimensioned and arranged to fit within a gingival sulcus of a patient, wherein the ultrasonic dental tip surface opposes a subgingival tooth surface.

14. The dental tool of claim 13, wherein the ultrasonic dental tip surface comprises a semi-permeable membrane, a glass frit, a semi-permeable fused ceramic, a woven fabric, a non-woven fabric, or a combination thereof.

15. The dental tool of claim 13, wherein the second end comprises a front side and an imperforate back side, the front side comprising the ultrasonic dental tip surface.

16. The dental tool of claim 15, wherein the ultrasonic dental tip surface comprises a planar surface.

17. The dental tool of claim 13, wherein the tip body comprises one or more swivel joints disposed between the first end and the second end to allow at least partial rotation of the second end relative to the first end.

18. The dental tool of claim 13, wherein at least a portion of the tip body comprises a flexible conduit disposed between the first end and the second end.

19. The dental tool of claim 13, further comprising a handpiece and a piezoelectric element, a magnetostrictive element, or a combination thereof.

20. The dental tool of claim 19, further comprising a control system comprising an ultrasonic power supply, a fluid supply in fluid communication with the internal fluid flow passage, a fluid supply pressure controller, a fluid supply flow rate controller, or a combination thereof.

21. The method of claim 1, wherein the surface of the dental tip is flat.

22. A method comprising:
inserting an ultrasonic oscillatory dental tip into the gingival sulcus of a patient to position a flat, porous ablating surface of the tip facing a subgingival tooth surface;
supplying a pressurized fluid through a plurality of openings in the ablating surface to form a fluid cushion to inhibit contact of the subgingival tooth surface by the ablating surface of the dental tip; and
while maintaining the fluid cushion between the ablating surface and the subgingival tooth surface, ultrasonically oscillating the dental tip to ablate biofilm from the tooth surface.

23. The method of claim 22, wherein the ablating surface of the tip is planar.

* * * * *